US00PP36518P2

(12) United States Plant Patent
Arotzarena et al.

(10) Patent No.: US PP36,518 P2
(45) Date of Patent: Mar. 4, 2025

(54) RASPBERRY PLANT NAMED 'Stella'

(50) Latin Name: ***Rubus idaeus* L**
Varietal Denomination: Stella

(71) Applicant: AROFA S.L., Tajonar (ES)

(72) Inventors: Domingo Arotzarena, Tajonar (ES); Francisco Román, Tajonar (ES); Antonio Soto, Tajonar (ES)

(73) Assignee: Arofa S.L., Tajonar (ES)

( * ) Notice: Subject to any disclaimer, the term of this patent is extended or adjusted under 35 U.S.C. 154(b) by 0 days.

(21) Appl. No.: 18/659,971

(22) Filed: May 9, 2024

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 6/7499; A01H 5/08
See application file for complete search history.

*Primary Examiner* — Keith O. Robinson
(74) *Attorney, Agent, or Firm* — Weatherly IP Solutions, LLC; James M. Weatherly

(57) ABSTRACT

A new raspberry plant named 'Stella' particularly distinguished by large fruit for use in fresh market, high brightness fruit; large number of branches after first crop, with a long cane; and good cold tolerance, is disclosed.

3 Drawing Sheets

Genus and species: *Rubus idaeus* L.
Variety denominations: 'Stella'.

BACKGROUND OF THE NEW PLANT 'STELLA'

The present invention comprises a new and distinct variety of Raspberry, botanically known as *Rubus idaeus* L, and hereinafter referred to by the variety name 'Stella'. 'Stella' originated from seed of a fruit from an unknown female and an unknown male plant. The seed was found in October 2018 in Applicant's fruit sorting and processing facility in Tarquejo, Huelva, Spain.

In October 2018, seed from the fruit found at Applicant's facility was planted. In October 2018 a plant was selected and named 'Stella'. 'Stella' was first vegetatively propagated by vegetative cuttings in Tarquejo, Huelva, Spain.

SUMMARY OF 'STELLA'

The following are the most outstanding and distinguishing characteristics of 'Stella' when grown under normal horticultural practices in Tarquejo, Huelva, Spain.

1. Large fruit for use in fresh market;
2. High brightness fruit;
3. Large number of branches after first crop, with a long cane; and
4. Good cold tolerance.

DESCRIPTION OF THE PHOTOGRAPHS

This new raspberry plant is illustrated by the accompanying photographs from October 2023 of plants grown in Tarquejo, Huelva, Spain. The plants are six months old and grown in a hydroponic system. The colors shown are as true as can be reasonably obtained by conventional photographic procedures.

DESCRIPTION OF 'STELLA'

Figure 1:
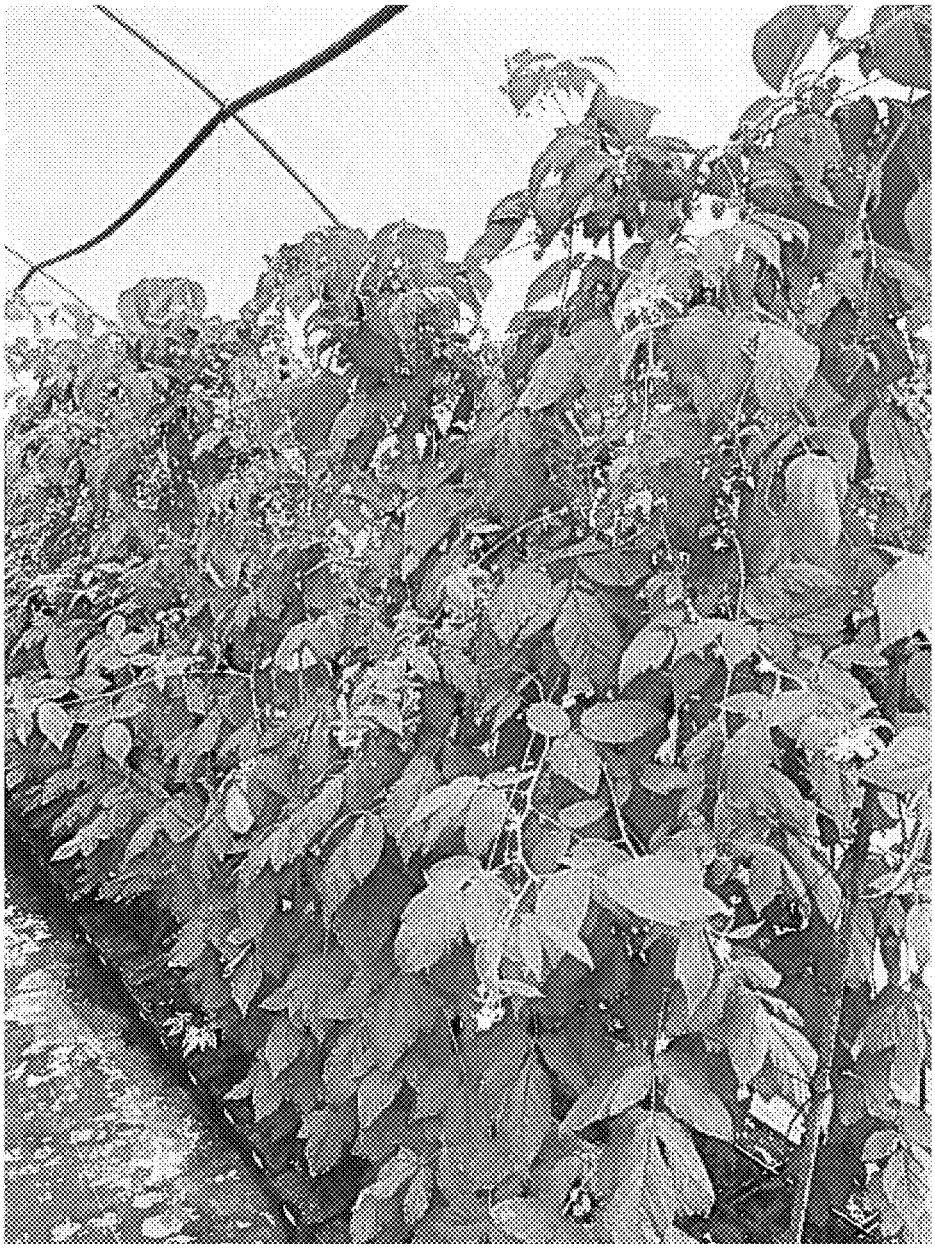
FIG. 1 shows a whole plant of 'Stella' showing foliage, buds, fruit and flowers.
Figure 2:
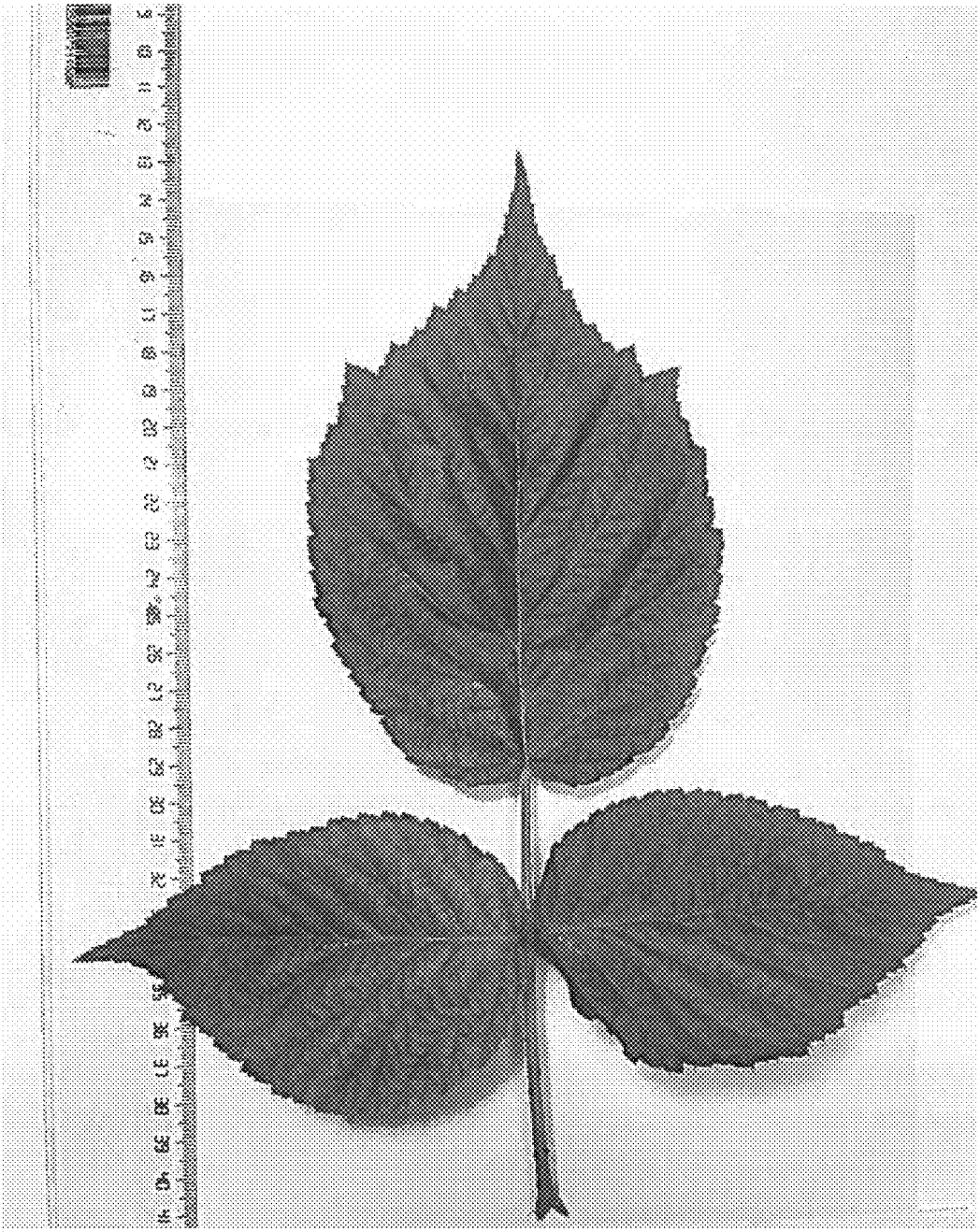
FIG. 2 shows the leaves of 'Stella'.
Figure 3:
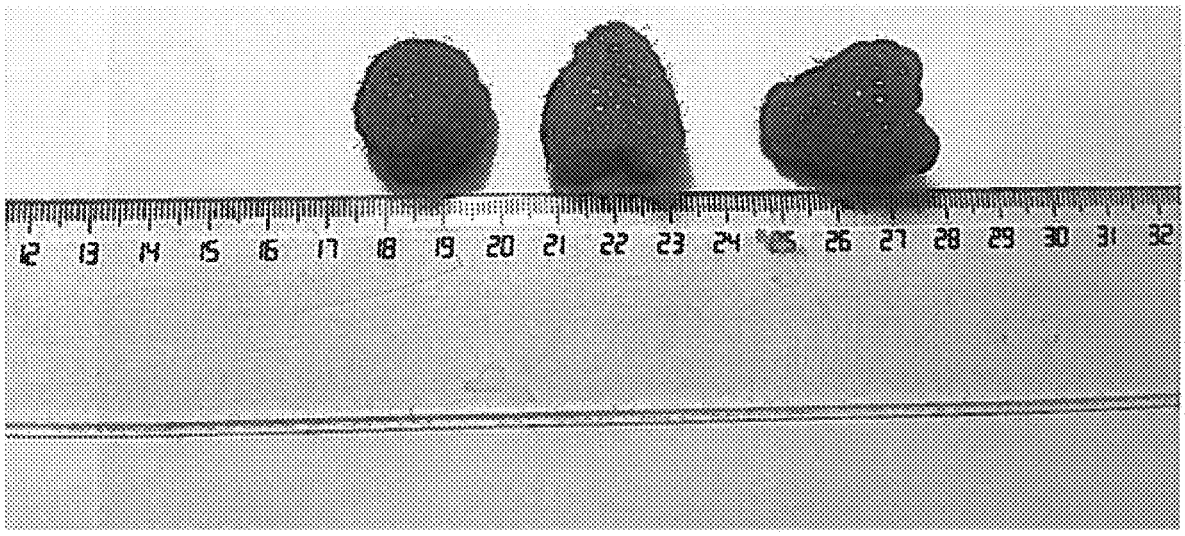
FIG. 3 shows the fruit of 'Stella'.

The following detailed descriptions set forth the distinctive characteristics of 'Stella'. The data which define these characteristics were collected from asexual reproductions carried out in Tariquejo, Huelva, Spain. Data was collected in 2022-2023 on 6-month old plants grown in a greenhouse in a hydroponic system. Color references are to The R.H.S. Colour Chart of The Royal Horticultural Society of London (R.H.S.), 6$^{th}$ edition (2015, reprint 2019).

Classification:
- *Family*.—Rosaceae.
- *Botanical*.—*Rubus idaeus* L.
- *Common*.—Raspberry.
- *Designation*.—'Stella'.

Plant:
- *Height*.—172 cm.
- *Width*.—40 cm.
- *Length/width ratio*.—4.3.
- *Growth habit*.—Semi-upright.

Primocane (current year's cane):
- *Number*.—Three.
- *Color*.—RHS 181C.
- *Cane length in autumn*.—172 cm.
- *Internodal distance at central ⅓ of cane*.—7.0 cm.
- *Anthocyanin coloration of cane*.—Medium.
- *Cane bloom*.—Medium.
- *Time of cane emergence*.—April 15$^{th}$.

Previous year canes:
- *Length of fruiting laterals*.—50.0 cm.
- *Time of beginning flowering on previous year's cane*.—Week 10.

*Time of beginning of fruit ripening on previous year's cane*.—Week 14.

*Time of vegetative bud burst*.—Week 6.

Very young shoot:

*Anthocyanin coloration of apex during rapid growth*.—RHS 149A.

Prickles (spines):

*Presence*.—Present.

*Density*.—Dense.

*Length at* 1 *in height at end of harvest* (*from base to tip*).—0.02 cm.

*Color*.—RHS N81A.

Leaves:

*Predominant number of leaflets*.—3.

*Profile of leaflets in cross section*.—Concave.

*Leaf rugosity*.—Weak.

*Color of upper side*.—RHS 144A.

*Color of lower side*.—RHS N148B.

*Surface texture of upper side*.—Smooth.

*Surface texture of lower side*.—A little rough.

*Terminal leaflet*.—Length: 17 cm. Width: 10 cm. Length/width ratio: 1.7. Margin: Undulate. Overall shape: Obovate. Apex shape: Acute. Base shape: Cordate.

*Lateral leaflets*.—Length: 10 cm. Width: 6 cm. Length/width ratio: 1.67. Arrangement of lateral leaflets: Free. Margin: Undulate. Overall shape: Lanceolate. Apex shape: Acute. Base shape: Rounded.

*Rachis length between terminal leaflet and adjacent lateral leaflets*.—4 cm.

*Petiole*.—Length: 11 cm. Diameter: 0.3 cm. Color: RHS N144D.

Flowers:

*Diameter*.—2 cm.

*Petal*.—Length: 0.8 cm. Width: 0.3 cm. Length/width ratio: 2.67. Color of upper side: RHS NN155A. Color of lower side: RHS NN155A.

*Sepal*.—Length: 2 cm. Width: 0.5 cm. Shape: Oblong. Color: RHS 145A.

*Pedicel*.—Length: 3 cm. Diameter: 0.1 cm. Color: RHS N144D. Surface texture: Thorny.

*Peduncle*.—Color: RHS N144D. Intensity of anthocyanin coloration: Weak. Surface texture: Thorny.

Fruit:

*Length*.—3 cm.

*Diameter*.—2.5 cm.

*Length/width ratio*.—1.2.

*General shape in lateral view*.—Conical.

*Color*.—RHS N30A.

*Glossiness*.—Strong.

*Firmness*.—Firm.

*Adherence to plug*.—Weak.

*Weight of single drupe*.—0.07 g.

*Number of drupelets per berry*.—100.

*Average weight per berry*.—5.5 g.

*Soluble solids* (° *brix*).—10.2.

Seed:

*Length*.—4 cm.

*Width*.—2 cm.

*Shape*.—Kidney.

*Color*.—RHS 24C.

Production:

*Main bearing type*.—Primocane.

*Primocane* (*current year's cane*).—Time of beginning of flowering: August 20th. Time of beginning of fruit ripening: September 20$^{th}$. Length of fruiting period: 3 months. Yield: 12000 kg to 16000 kg per hectare per season from 6-month-old plants when grown in Huelva (Spain). Fruit storage life and shipping quality: 10 days. Market use: Fresh. Heat/cold tolerance: Both cold and heat tolerance. Plant/fruit disease and pest resistance/susceptibility: None.

'Stella' can be compared to the commercial Raspberry variety 'RAFZAQU' (U.S. Plant Pat. No. 19,512). Differences between the varieties are described in Table 1.

TABLE 1

| Comparison with Similar Variety | Variety 'Stella' | Commercial line 'RAFZAQU' |
|---|---|---|
| Winter production | Yes | No |
| Fruit color | N30A | 44A |
| Internodal distance | 7 cm | 4.5 cm |
| Plant height | 172 cm | 156 cm |
| Thorn color | N81A | 183A |
| Primocane cane color | 181C | 144B |

I claim:

1. A new and distinct variety of raspberry plant named 'Stella', as illustrated and described herein.

* * * * *